United States Patent
Fan et al.

(10) Patent No.: US 12,044,762 B2
(45) Date of Patent: Jul. 23, 2024

(54) ESTIMATING DIFFUSION METRICS FROM DIFFUSION- WEIGHTED MAGNETIC RESONANCE IMAGES USING OPTIMIZED K-Q SPACE SAMPLING AND DEEP LEARNING

(71) Applicant: THE GENERAL HOSPITAL CORPORATION, Boston, MA (US)

(72) Inventors: Qiuyun Fan, Malden, MA (US); Susie Yi Huang, Boston, MA (US); Qiyuan Tian, Charlestown, MA (US); Chanon Ngamsombat, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 721 days.

(21) Appl. No.: 17/166,734

(22) Filed: Feb. 3, 2021

(65) Prior Publication Data

US 2021/0239780 A1     Aug. 5, 2021

Related U.S. Application Data

(60) Provisional application No. 62/969,478, filed on Feb. 3, 2020.

(51) Int. Cl.
| | |
|---|---|
| *G01R 33/563* | (2006.01) |
| *G01R 33/48* | (2006.01) |
| *G01R 33/56* | (2006.01) |
| *G06N 3/08* | (2023.01) |
| *G06T 11/00* | (2006.01) |
| *G16H 30/40* | (2018.01) |

(52) U.S. Cl.
CPC ... *G01R 33/56341* (2013.01); *G01R 33/4818* (2013.01); *G01R 33/5608* (2013.01); *G06N 3/08* (2013.01); *G06T 11/008* (2013.01); *G16H 30/40* (2018.01)

(58) Field of Classification Search
None
See application file for complete search history.

(56) References Cited

PUBLICATIONS

HIgh b-value and high Resolution Integrated Diffusion (HIBRID) imaging. Fan et al. (Year: 2017).*
Multi-Shot Multi-Channel Diffusion Data Recovery Using Structured Low-Rank Matrix Completion. Mani et al. (Year: 2016).*
Cross-scanner and cross-protocol diffusion MRI data harmonisation: A benchmark database and evaluation of algorithms. Tax et al. (Year: 2019).*
Fan, Q. et al., "High b-value and high Resolution Integrated Diffusion (Hybrid) imaging," Neuroimage, 2017; 150:162-176.

* cited by examiner

*Primary Examiner* — Delomia L Gilliard
(74) *Attorney, Agent, or Firm* — Quarles & Brady LLP (57) ABSTRACT

Diffusion metric maps are generated from a limited input of magnetic resonance data to a suitably trained machine learning algorithm, such as a suitably trained neural network. In general, a downsampling strategy is implemented in the joint k-q space to enable the simultaneous estimation of multiple different diffusion metrics from a more limited set of input diffusion-weighted images.

19 Claims, 6 Drawing Sheets

ESTIMATING DIFFUSION METRICS FROM DIFFUSION-WEIGHTED MAGNETIC RESONANCE IMAGES USING OPTIMIZED K-Q SPACE SAMPLING AND DEEP LEARNING

CROSS-REFERENCE TO RELATED APPLICATIONS

This application claims the benefit of U.S. Provisional Patent Application Ser. No. 62/969,478, filed on Feb. 3, 2020, and entitled "ESTIMATING MICROSTRUCTURAL METRICS FROM NINE DIFFUSION-WEIGHTED IMAGES USING OPTIMIZED K-Q SPACE SAMPLING AND DEEP LEARNING."

STATEMENT REGARDING FEDERALLY SPONSORED RESEARCH

This invention was made with government support under EB026996 awarded by the National Institutes of Health. The government has certain rights in the invention.

BACKGROUND

Conventional imaging protocols that are capable of generating reliable maps of neurite orientation dispersion and density imaging ("NODDI") or other advanced diffusion models usually require tens or hundreds of samples in q-space, which renders the acquisition too time-consuming to be clinical feasible. While k-space and q-space redundancy have long been recognized, analytically modeling the 6D joint k-q space for microstructural imaging to take advantage of this redundancy is challenging. Recent studies that achieved either super-resolution in the "k"-dimension or heavy down-sampling in the "q"-dimension alone have demonstrated the promise of deep learning in sparse acquisition sampling schemes. In practice, image SNR decreases as either k or q increases, motivating the sought after the High B-value and high Resolution Integrated Diffusion ("HIBRID") acquisition to take the advantages of high k and high q simultaneously.

SUMMARY OF THE DISCLOSURE

The present disclosure addresses the aforementioned drawbacks by providing a method for generating diffusion metric maps from magnetic resonance data. The method includes accessing magnetic resonance data with a computer system, the magnetic resonance data being acquired from a subject, The magnetic resonance data include first data that sample k-space with a first k-space sampling and sample q-space with a first q-space sampling, and second data that sample k-space with a second k-space sampling and sample q-space with a second q-space sampling, where the first k-space sampling is higher than the second k-space sampling, and the first q-space sampling is lower than the second q-space sampling. A trained neural network is accessed with the computer system, where the trained neural network has been trained on training data in order to learn a mapping from magnetic resonance data to diffusion metrics corresponding to at least two different diffusion models. The magnetic resonance data are then input to the trained neural network using the computer system, generating output as a plurality of diffusion metric maps, where the plurality of diffusion metric maps depict a spatial distribution in the subject of the diffusion metrics corresponding to the at least two different diffusion models.

It is another aspect of the present disclosure to provide a method for generating diffusion metric maps from magnetic resonance data acquired with a magnetic resonance imaging (MRI) system. The method includes acquiring diffusion-weighted magnetic resonance data from a subject with the MRI system, where the diffusion-weighted magnetic resonance data jointly sample k-q space such that k-space sampling is increased at lower diffusion weighting b-values and q-space sampling is increased at lower spatial resolutions. Diffusion-weighted images are reconstructed from the diffusion-weighted magnetic resonance data using a computer system. A trained neural network is also accessed with the computer system, where the trained neural network has been trained on training data in order to learn a mapping from diffusion-weighted images to diffusion metrics corresponding to at least two different diffusion models. The diffusion-weighted images are then input to the trained neural network using the computer system, generating output as a plurality of diffusion metric maps, where the plurality of diffusion metric maps depict a spatial distribution in the subject of the diffusion metrics corresponding to the at least two different diffusion models.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Described here are systems and methods for generating diffusion metric maps from a limited input of magnetic resonance data to a suitably trained machine learning algorithm, such as a suitably trained neural network. In general, the systems and methods provide a downsampling strategy in the joint k-q space to enable the simultaneous estimation of multiple different diffusion metrics from a more limited set of input diffusion-weighted images.

In some embodiments, data are acquired while condensing the k-q space jointly, and diffusion metric maps are generated using a deep convolutional neural network ("CNN"). For example, data can be acquired using a high b-value and high resolution integrated diffusion ("HIBRID") acquisition. In some implementations, the acquired data can include two datasets: a high-k dataset with high k-space sampling and low q-space sampling, and a high-q dataset with low k-space sampling and high q-space sampling. Additionally or alternatively, datasets with other ratios of k-space sampling-to-q-space sampling can also be acquired, where the joint sampling in k-q space is optimized to condense the k-q joint space. In such instances, the systems and methods may be referred to as using a "DeepHIBRID" network.

As a non-limiting example, 10 diffusion-weighted images can be used to estimate 14 maps of microstructural metrics simultaneously, achieving both denoising and super-resolution using a deep 3D CNN. This represents a significant improvement over conventional model fitting approaches, which are incapable of generating such outputs based on the more limited inputs described in the present disclosure. For instance, the microstructural maps synthesized using the systems and methods described in the present disclosure achieve comparable performance with upwards of thirty-fold fewer less samples in q-space compared to conventional fully sampled diffusion MRI data. As a result, the systems and methods described in the present disclosure are able to avoid the long acquisition time required to obtain the data necessary for conventional model fitting approaches, and therefore decrease the scan cost while increasing the motion robustness of the scan and improving patient comfort. Advantageously, the systems and methods described in the present disclosure can also be directly applied to previously acquired datasets that have been acquired at lower spatial or angular resolution.

As noted above, the systems and methods described in the present disclosure generate as output a number of different maps of microstructural diffusion metrics. In general, these different diffusion metrics are representative of different models. Advantageously, these multiple different diffusion metric maps can be simultaneously generated from a reduced quantity of data, thereby allowing for acquisition time to be significantly decreased. The output diffusion metric maps can provide microstructural parameters for clinical purposes of diagnosis, prognosis, and treatment, in addition to scientific purposes in neuroscientific, neurological, neurosurgical, psychiatric, and psychological research.

The DeepHIBRID network described in the present disclosure performs simultaneous denoising and super-resolution by leveraging the data redundancy in the k-q joint space. As described, in a non-limiting example, the DeepHIBRID network is capable of generating 14 channels of output maps with only 10 channels of input images, which is indicative of the great degree of redundancy not only in the k-q joint space on the input side, but also in the parameter maps on the output side.

Figure 1:
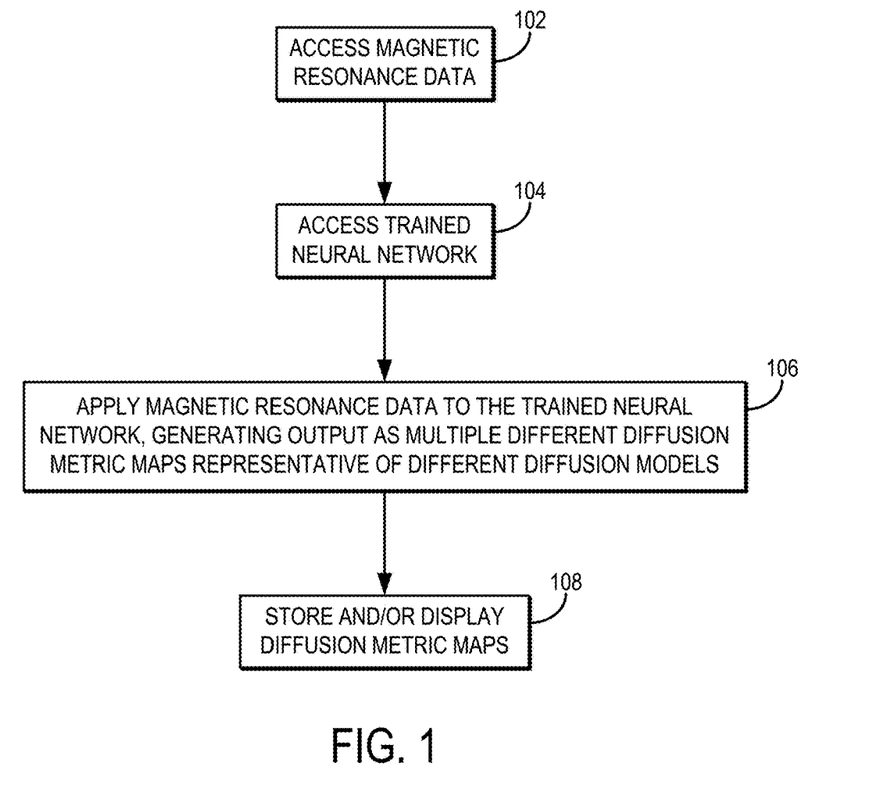
FIG. 1 is a flowchart setting forth the steps of an example method for simultaneously generating diffusion metric maps representative of two or more different diffusion models using magnetic resonance data input to a trained neural network.

Referring now to FIG. 1, a flowchart is illustrated as setting forth the steps of an example method for simultaneously generating multiple different diffusion metrics maps representative of different diffusion models based on inputting jointly condensed k-q space data to a suitably trained neural network or other machine learning algorithm.

The method includes accessing magnetic resonance data with a computer system, as indicated at step 102. Accessing the magnetic resonance data may include retrieving such data from a memory or other suitable data storage device or medium. Alternatively, accessing the magnetic resonance data may include acquiring such data with an MRI system and transferring or otherwise communicating the data to the computer system, which may be a part of the MRI system.

In general, the magnetic resonance data include diffusion-weighted data that are acquired using an optimized k-q space sampling, such as jointly condensed k-q space data. For instance, the diffusion-weighted data can be acquired using a so-called high b-value and high resolution integrated diffusion ("HIBRID") imaging technique. In such a technique, the diffusion-weighted data are acquired such that data acquired at higher spatial resolution (k) will have lower diffusion weighting (q), and data acquired at higher diffusion weighting (q) will have lower spatial resolution (k).

Figure 2:
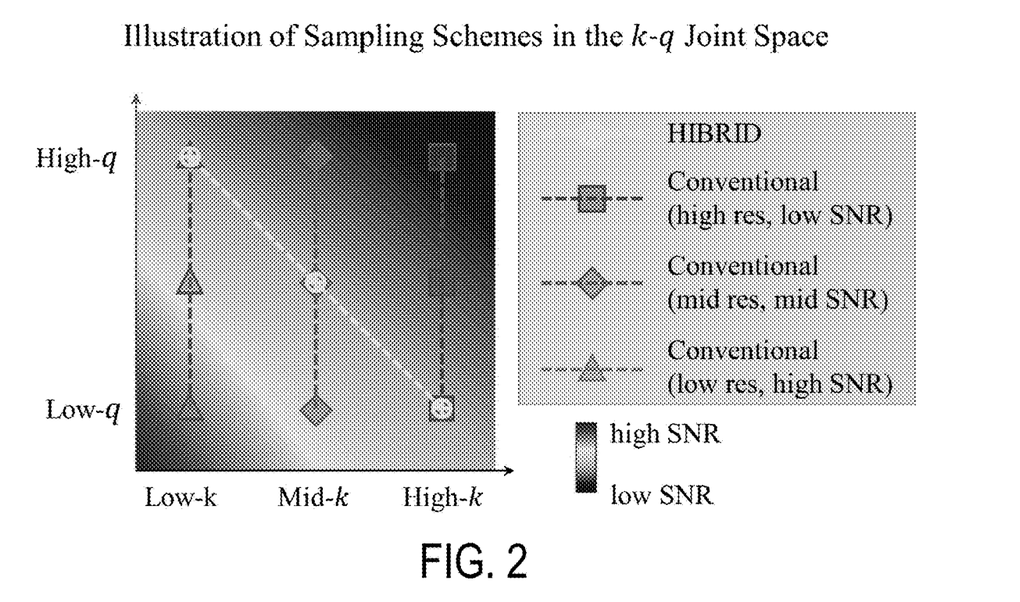
FIG. 2 illustrates example k-q space sampling schemes that can be implemented in some embodiments described in the present disclosure.

An example of a HIBRID and other sampling schemes in k-q joint space is illustrated in FIG. 2. Image SNR depends on spatial resolution (k) and diffusion weighting (q). Conventionally, multi-shell diffusion data are acquired with fixed spatial resolution (k), as illustrated by the Low-k (marked in triangles), Mid-k (diamonds), and High-k (squares) protocols, with their corresponding pros and cons in resolution and SNR. The HIBRID imaging sampling scheme is motivated by the SNR trade-offs, and acquires lower shells with higher spatial resolution, and higher shells with lower resolution.

In some instances, data acquired with a HIBRID acquisition strategy can include two complementary datasets: one that pushes the limits of k-space sampling (i.e., high resolution) by compromising q-space sampling, and one that pushes the limits of q-space sampling (i.e., high b-value, or diffusion weighting) by compromising k-space sampling. These datasets may be referred to as high k-space and high q-space datasets, respectively.

In some implementations, the high k-space and high q-space datasets can then be integrated by performing a fusion of the two datasets, which may be performed on the orientation distribution functions ("ODFs"). For instance, a HIBRID ODF can be calculated as a weighted sum of the ODFs obtained from the two datasets separately. As one example, the weights can be spatially variant weights based on a distance metric calculated for each voxel. In one non-limiting example, the diffusion metric can be a three-dimensional Euclidean distance calculated between each voxel and a boundary surface, such as a white-gray matter boundary. In general, closer to the cortex, the ODFs obtained from the high k-space dataset will be more heavily weighted, and further into white matter, the ODFs obtained from the high q-space dataset will be more heavily weighted. Examples of how such weights can be calculated are described by Q. Fan, et al., in "High b-value and high Resolution Integrated Diffusion (HIBRID) imaging," Neuroimage, 2017; 150:162-176 which is herein incorporated by reference in its entirety.

As one non-limiting example, the magnetic resonance data can include diffusion-weighted data acquired over a number of diffusion weighting b-values. For instance, the magnetic resonance data may include diffusion data acquired at b=1000, 2000, and 3000 s/mm$^2$ shells, each with 90 uniform encoding directions and 18 interspersed b=0 volumes. In such instances, the magnetic resonance data may then include a single b=0 image and three diffusion-weighted images along orthogonal directions from each shell, for a total of 10 input channels.

By implementing a HIBRID sampling strategy, the diffusion-weighted data acquired with higher b-values are acquired at lower spatial resolution, and the diffusion-weighted data acquired with lower b-values are acquired at higher spatial resolution. Thus, in the example described above, the diffusion-weighted data acquired with a b-value of 1000 mm/s$^2$ are acquired with higher spatial resolution than the diffusion-weighted data acquired with a b-value of 3000 mm/s$^2$.

It will be appreciated that the magnetic resonance data may include diffusion-weighted acquired for fewer than three b-values, or for more than three b-values. Similarly, the diffusion-weighted data may be acquired for b-values other than 1000, 2000, and 3000 mm/s$^2$. As an example, diffusion-weighted data may be acquired for b-values from 0 mm/s$^2$ and up to 8000 mm/s$^2$. Thus, b-values may include values such as 10 mm/s$^2$, 20 mm/s$^2$, 30 mm/s$^2$, 40 mm/s$^2$, 50 mm/s$^2$, etc., or values therebetween; values such as 100 mm/s$^2$, 200 mm/s$^2$, 300 mm/s$^2$, 400 mm/s$^2$, 500 mm/s$^2$, etc., or values therebetween; and/or values such as 1000 mm/s$^2$, 2000 mm/s$^2$, 3000 mm/s$^2$, 4000 mm/s$^2$, 5000 mm/s$^2$, etc., or values therebetween.

A trained neural network (or other suitable machine learning algorithm) is then accessed with the computer system, as indicated at step 104. Accessing the trained neural network may include accessing network parameters (e.g., weights, biases, or both) that have been optimized or otherwise estimated by training the neural network on training data. In some instances, retrieving the neural network can also include retrieving, constructing, or otherwise accessing the particular neural network architecture to be implemented. For instance, data pertaining to the layers in the neural network architecture (e.g., number of layers, type of layers, ordering of layers, connections between layers, hyperparameters for layers) may be retrieved, selected, constructed, or otherwise accessed.

In general, the neural network is trained, or has been trained, on training data in order to estimate multiple different diffusion metrics and/or diffusion metric maps based on several different diffusion models.

Figure 3:
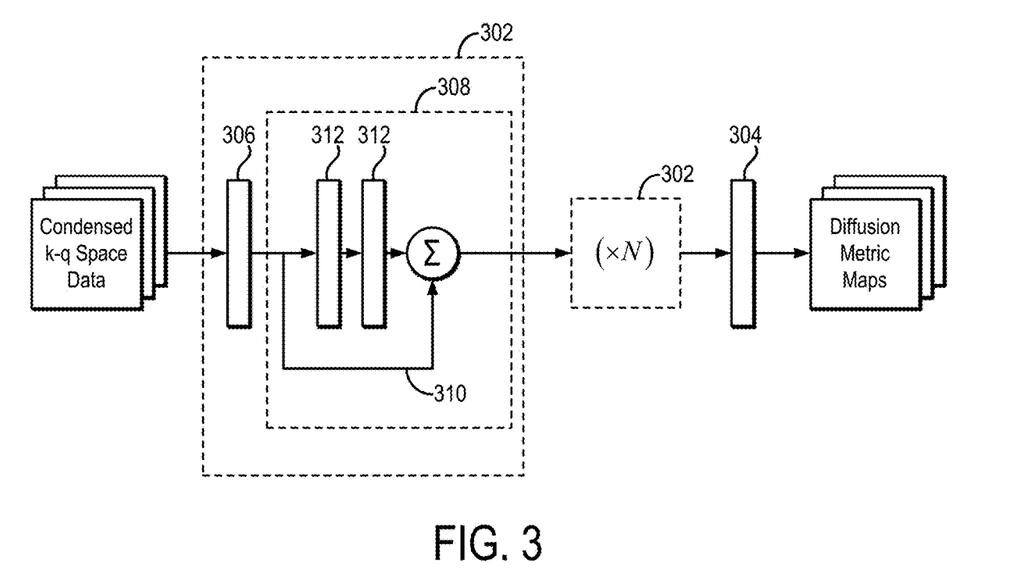
FIG. 3 is an example of a three-dimensional deep residual network convolutional neural network architecture that can be implemented in some embodiments described in the present disclosure.

As one example, the neural network can be a deep 3D ResNet CNN, such as the one shown in FIG. 3. As shown, this neural network 300 includes a plurality of network stages 302 and an output layer 304. For instance, the neural network 300 can include N+1 network stages 302, where the output of the first network stage 302 is applied as an input to the next network stage 302, which is repeated N times until the output of the last network stage 302 is input to the output layer 304.

Each network stage 302 includes an input block 306 followed by a residual block 308. The residual block 308 includes a skip connection 310 that takes the output of the input block 306 and applies it to a deeper layer of the network 300. For example, the skip connection takes the output of the input block 306, sums it with the output of the residual block 308, and applies the sum to the next layer of the network, which may be the input block 306 of the next network stage 302 or the output layer 304.

In general, each input block 306 includes a three-dimensional convolution layer, followed by a batch normalization layer, followed by an activation layer. The activation layer may implement a rectified linear unit ("ReLU") or other nonlinear activation function.

Each residual block 308 is composed of two or more sub-blocks 312. Like the input block 306, each sub-block 312 includes a three-dimensional convolution layer, followed by a batch normalization layer, followed by an activation layer. The convolution layers in the sub-blocks 312 generally have larger kernels than the convolution layers in the input blocks 306. For instance, the convolution layers in the input block 306 may have 1×1 kernels, whereas the convolution layers in the sub-blocks 312 may have 3×3 kernels.

Generally, the layers in each successive network stage 302 will have an increasing number of channels. For instance, in the example shown in FIG. 3, the network 300 has four network stages 302 and an output layer 304. The first network stage 302 may have 64 channels, the second network stage 302 may have 128 channels, the third network stage 302 may have 192 channels, and the fourth network stage 302 may have 256 channels.

Referring again to FIG. 1, the magnetic resonance data are then input to the one or more trained neural networks, generating output as diffusion metric maps, as indicated at step 106. As described above, in one non-limiting example, the magnetic resonance data input to the trained neural network can include ten total inputs: a single b=0 image and three diffusion-weighted images acquired for three different non-zero b-values. For instance, the first three diffusion-encoding directions in each of three different shells can be selected, such that the directions are largely uniformly distributed on the sphere of the shell.

The output diffusion metric maps correspond to diffusion metrics from two or more different diffusion models. For example, the diffusion metric maps are representative of multiple different diffusion models, such as diffusion tensor imaging ("DTI") model, neurite orientation dispersion and density imaging ("NODDI") model, spherical mean technique ("SMT") micro-diffusion tensor ("microDT") model, and/or SMT multi-compartment microstructural imaging ("SMT McMicro") model.

The diffusion metric maps depict the spatial distribution or spatial patterns of diffusion metrics. As one non-limiting example, the diffusion metrics may include DTI-model based metrics, such as fractional anisotropy ("FA"), mean diffusivity ("MD"), axial diffusivity ("AD"), radial diffusivity ("RD"), and/or other DTI-model based diffusion metrics. Additionally or alternatively, the diffusion metrics may include NODDI-model based metrics, such as fraction of water in the restricted compartment ("ficvf"), fraction of water in the isotropic compartment ("fiso"), orientation dispersion index ("ODI"), hindered volume fraction ("fh"), where fh=1—ficvf—fiso, and/or other NODDI-model based diffusion metrics. As still another non-limiting example, the diffusion metrics may include SMT microDT-model based metrics, such as FA, MD, RD, and/or other SMT microDT-model based diffusion metrics. Additionally or alternatively, the diffusion metrics may include SMT McMicro-model based metrics, such as intra-axonal water fraction ("fintra"), extra-neurite microscopic mean diffusivity ("extraMD"), extra-neurite transverse microscopic diffusivity ("extraTrans"), and/or other SMT McMicro-model based diffusion metrics.

The diffusion metric maps generated by inputting the magnetic resonance data to the trained neural network(s) can then be displayed to a user, stored for later use or further processing, or both, as indicated at step 108.

Figure 4:
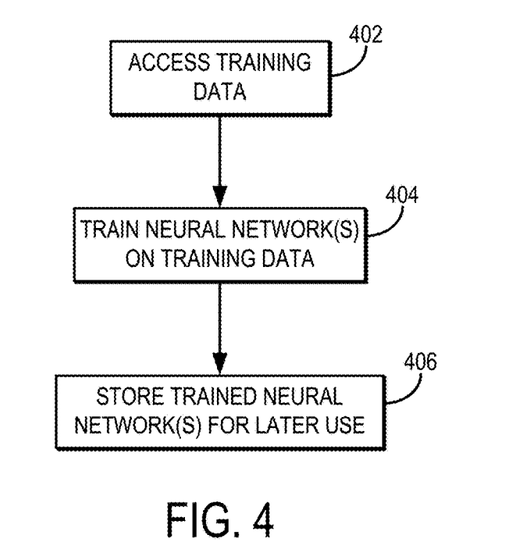
FIG. 4 is a flowchart setting forth the steps of an example method for training a neural network in accordance with some embodiments described in the present disclosure.

Referring now to FIG. 4, a flowchart is illustrated as setting forth the steps of an example method for training one or more neural networks (or other suitable machine learning algorithms) on training data, such that the one or more neural networks are trained to receive input as magnetic resonance data in order to generate output as diffusion metric maps representative of multiple different diffusion models (e.g., DTI, NODDI, SMT MicroDT, SMT McMicro).

In general, the neural network(s) can implement any number of different neural network architectures. For instance, the neural network(s) could implement a convolutional neural network, a residual neural network, or other suitable neural network architecture.

Alternatively, the neural network(s) could be replaced with other suitable machine learning algorithms, such as those based on supervised learning, unsupervised learning, deep learning, ensemble learning, dimensionality reduction, and so on.

Figure 5:
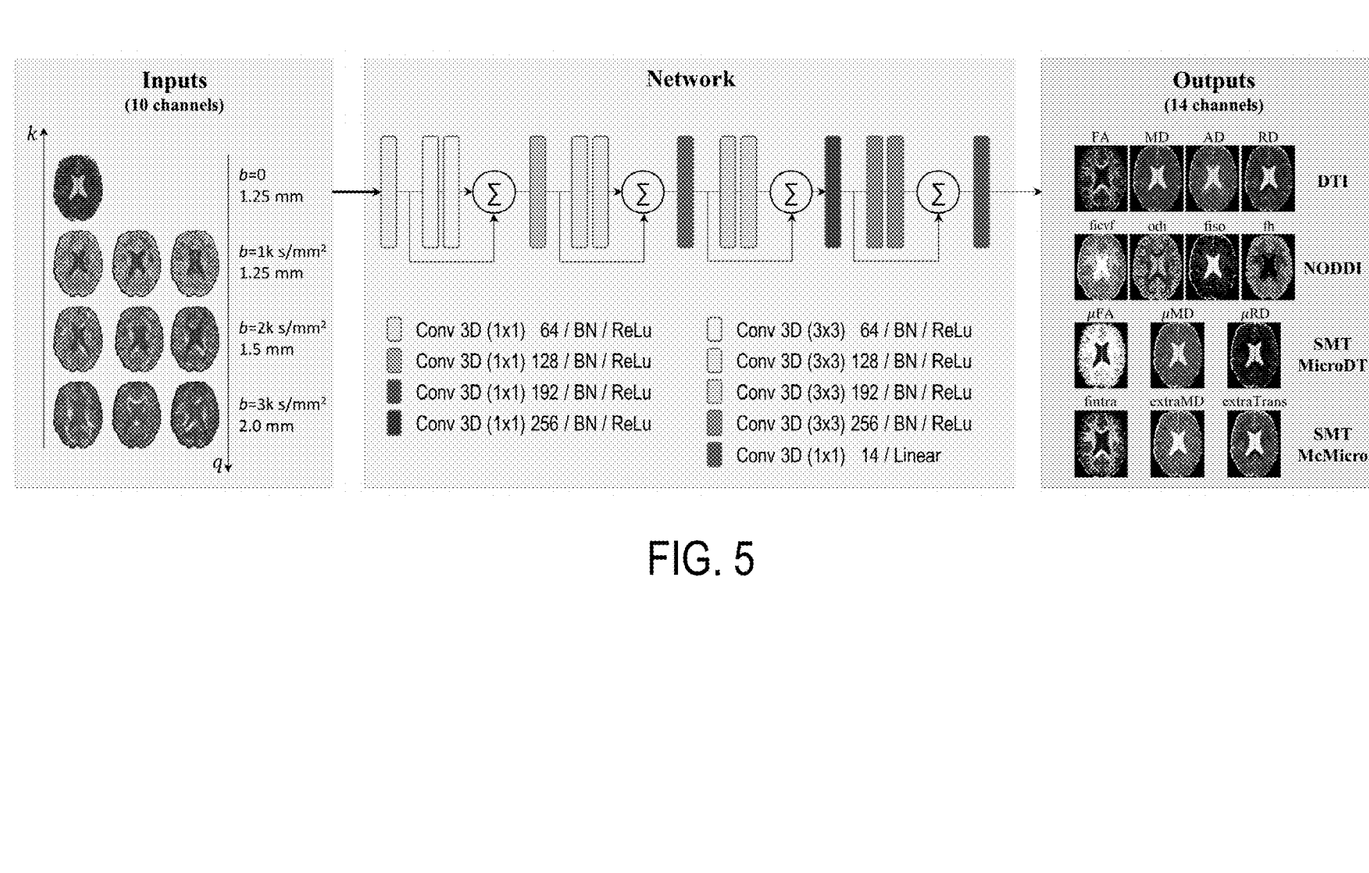
FIG. 5 illustrates an example implementation of a three-dimensional deep residual network convolutional neural network for generating 14 different diffusion metric maps representative of four different diffusion models from an input of 10 diffusion-weighted images representative of one b=0 image and three images each at three different b-values.

As described above, in a non-limiting example, the neural network to be trained can be a 3D ResNet CNN, such as the one shown in FIG. 3. A specific example of this network architecture is shown in FIG. 5, which depicts the layout of the network and its inputs and outputs. A 3D CNN is used, with increased number of filters in deeper layers. The input layer takes 10 channels, which includes one $b=0$ mm/s$^2$ image, $3b=$mm/s$^2$ images, three $b=2000$ mm/s$^2$ images, and three $b=3000$ mm/s$^2$ images. The output layer gives 14 synthesized maps of microstructural diffusion metrics, representative of the outputs from the DTI, NODDI, Spherical Mean Technique (SMT) micro-Diffusion Tensor (microDT), and SMT Multi-compartment Microstructural imaging (SMT McMicro) models.

The method includes accessing training data with a computer system, as indicated at step 402. Accessing the training data may include retrieving such data from a memory or other suitable data storage device or medium. Alternatively, accessing the training data may include acquiring such data with an MRI and transferring or otherwise communicating the data to the computer system, which may be a part of the MRI.

In general, the training data can include diffusion-weighted magnetic resonance data. For instance, the training data may include magnetic resonance data acquired using a number of different diffusion-weightings and/or encoding strategies. Additionally or alternatively, the training data may include ground-truth diffusion metric maps for learning a mapping from the input magnetic resonance data to the ground-truth diffusion metric maps.

Additionally or alternatively, the method can include assembling training data from magnetic resonance data and/or ground-truth diffusion metric maps using a computer system. This step may include assembling the magnetic resonance data into an appropriate data structure on which the neural network or other machine learning algorithm can be trained. Assembling the training data may include assembling magnetic resonance data, ground-truth diffusion metric maps, and other relevant data.

Assembling the training data may also include implementing a data augmentation process in order to generate cloned data from the magnetic resonance data and/or ground-truth diffusion metric maps. As an example, the cloned data can be generated by making copies of the magnetic resonance data while altering or modifying each copy of the magnetic resonance data. For instance, cloned data can be generated using data augmentation techniques, such as adding noise to the original magnetic resonance data, performing a deformable transformation (e.g., translation, rotation, both) on the original magnetic resonance data, smoothing the original magnetic resonance data, applying a random geometric perturbation to the original magnetic resonance data, combinations thereof, and so on.

One or more neural networks (or other suitable machine learning algorithms) are trained on the training data, as indicated at step 404. In general, the neural network can be trained by optimizing network parameters (e.g., weights, biases, or both) based on minimizing a loss function. As one non-limiting example, the loss function may be a mean squared error loss function.

Training a neural network may include initializing the neural network, such as by computing, estimating, or otherwise selecting initial network parameters (e.g., weights, biases, or both). Training data can then be input to the initialized neural network, generating output as diffusion metric maps. The quality of the diffusion metric maps can then be evaluated, such as by passing the output diffusion metric maps to a loss function to compute an error. The current neural network can then be updated based on the calculated error (e.g., using backpropagation methods based on the calculated error). For instance, the current neural network can be updated by updating the network parameters (e.g., weights, biases, or both) in order to minimize the loss according to the loss function. When the error has been minimized (e.g., by determining whether an error threshold or other stopping criterion has been satisfied), the current neural network and its associated network parameters represent the trained neural network.

The one or more trained neural networks are then stored for later use, as indicated at step 406. Storing the neural network(s) may include storing network parameters (e.g., weights, biases, or both), which have been computed or otherwise estimated by training the neural network(s) on the training data. Storing the trained neural network(s) may also include storing the particular neural network architecture to be implemented. For instance, data pertaining to the layers in the neural network architecture (e.g., number of layers, type of layers, ordering of layers, connections between layers, hyperparameters for layers) may be stored.

Figure 6:
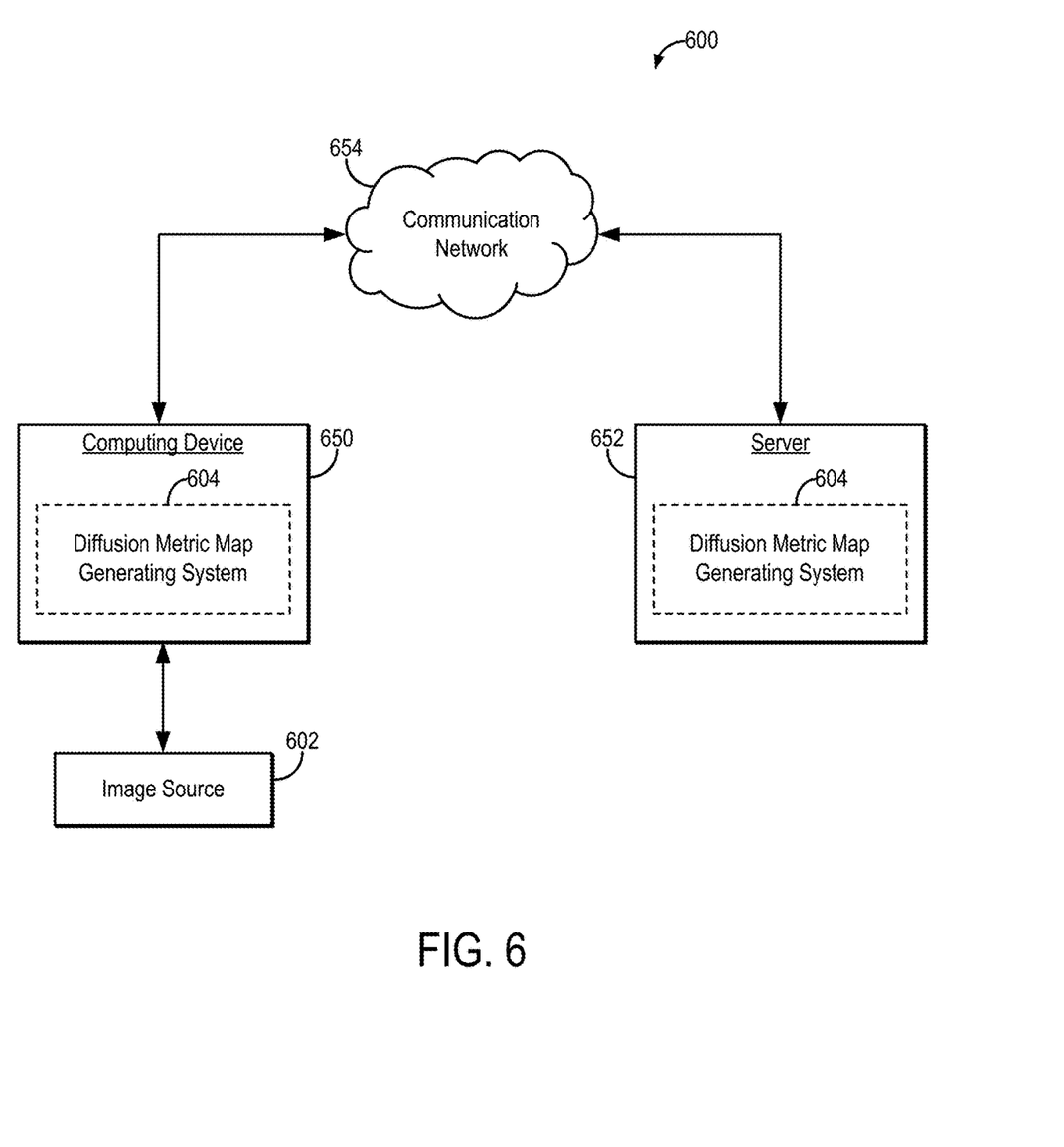
FIG. 6 is a block diagram of an example system that can be implemented for generating diffusion metric maps.

Referring now to FIG. 6, an example of a system 600 for generating diffusion metric maps in accordance with some embodiments of the systems and methods described in the present disclosure is shown. As shown in FIG. 6, a computing device 650 can receive one or more types of data (e.g., magnetic resonance data, which may be representative of condensed k-q joint space data) from image source 602, which may be a magnetic resonance image source. In some embodiments, computing device 650 can execute at least a portion of a diffusion metric map generating system 604 to simultaneously generate multiple different diffusion metric maps from data received from the image source 602, where the diffusion metrics are representative of two or more different diffusion models.

Additionally or alternatively, in some embodiments, the computing device 650 can communicate information about data received from the image source 602 to a server 652 over a communication network 654, which can execute at least a portion of the diffusion metric map generating system 604. In such embodiments, the server 652 can return information to the computing device 650 (and/or any other suitable computing device) indicative of an output of the diffusion metric map generating system 604.

In some embodiments, computing device 650 and/or server 652 can be any suitable computing device or combination of devices, such as a desktop computer, a laptop computer, a smartphone, a tablet computer, a wearable computer, a server computer, a virtual machine being executed by a physical computing device, and so on. The computing device 650 and/or server 652 can also reconstruct images from the data.

In some embodiments, image source 602 can be any suitable source of image data (e.g., measurement data, images reconstructed from measurement data), such as an MRI system, another computing device (e.g., a server storing image data), and so on. In some embodiments, image source 602 can be local to computing device 650. For example, image source 602 can be incorporated with computing device 650 (e.g., computing device 650 can be configured as part of a device for capturing, scanning, and/or storing images). As another example, image source 602 can be connected to computing device 650 by a cable, a direct wireless link, and so on. Additionally or alternatively, in some embodiments, image source 602 can be located locally and/or remotely from computing device 650, and can communicate data to computing device 650 (and/or server 652) via a communication network (e.g., communication network 654).

In some embodiments, communication network 654 can be any suitable communication network or combination of communication networks. For example, communication network 654 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 654 can be a local area network, a wide area network, a public network (e.g., the Internet), a private or semi-private network (e.g., a corporate or university intranet), any other suitable type of network, or any suitable combination of networks. Communications links shown in FIG. 6 can each be any suitable communications link or combination of communications links, such as wired links, fiber optic links, Wi-Fi links, Bluetooth links, cellular links, and so on.

Figure 7:
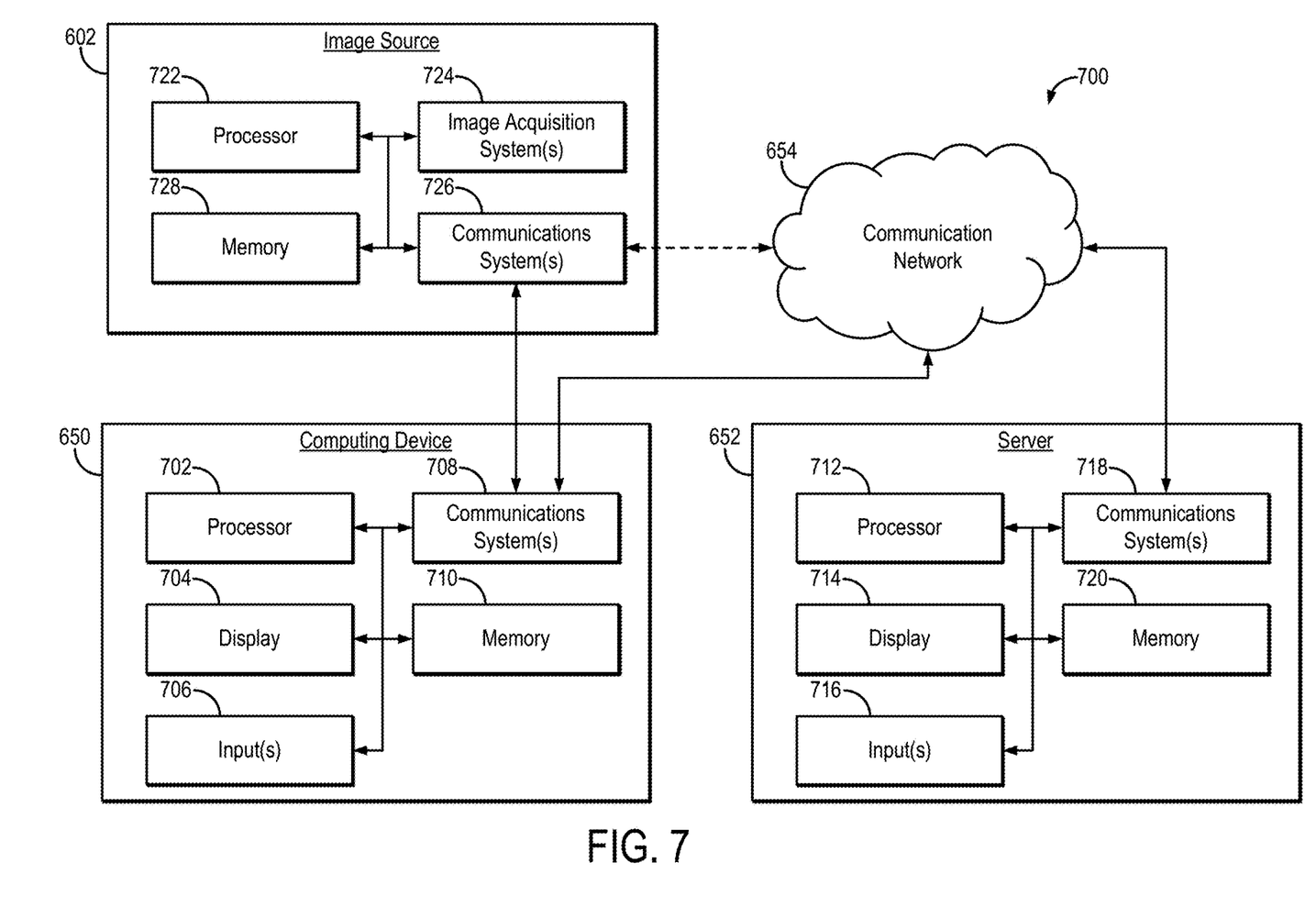
FIG. 7 is a block diagram of example components that can implement the system of FIG. 6.

Referring now to FIG. 7, an example of hardware 700 that can be used to implement image source 602, computing device 650, and server 652 in accordance with some embodiments of the systems and methods described in the present disclosure is shown. As shown in FIG. 7, in some embodiments, computing device 650 can include a processor 702, a display 704, one or more inputs 706, one or more communication systems 708, and/or memory 710. In some embodiments, processor 702 can be any suitable hardware processor or combination of processors, such as a central processing unit ("CPU"), a graphics processing unit ("GPU"), and so on. In some embodiments, display 704 can include any suitable display devices, such as a computer monitor, a touchscreen, a television, and so on. In some embodiments, inputs 706 can include any suitable input devices and/or sensors that can be used to receive user input, such as a keyboard, a mouse, a touchscreen, a microphone, and so on.

In some embodiments, communications systems 708 can include any suitable hardware, firmware, and/or software for communicating information over communication network 654 and/or any other suitable communication networks. For example, communications systems 708 can include one or more transceivers, one or more communication chips and/or chip sets, and so on. In a more particular example, communications systems 708 can include hardware, firmware and/or software that can be used to establish a Wi-Fi connection, a Bluetooth connection, a cellular connection, an Ethernet connection, and so on.

In some embodiments, memory 710 can include any suitable storage device or devices that can be used to store instructions, values, data, or the like, that can be used, for example, by processor 702 to present content using display 704, to communicate with server 652 via communications system(s) 708, and so on. Memory 710 can include any suitable volatile memory, non-volatile memory, storage, or any suitable combination thereof. For example, memory 710 can include RAM, ROM, EEPROM, one or more flash drives, one or more hard disks, one or more solid state drives, one or more optical drives, and so on. In some embodiments, memory 710 can have encoded thereon, or otherwise stored therein, a computer program for controlling operation of computing device 650. In such embodiments, processor 702 can execute at least a portion of the computer program to present content (e.g., images, user interfaces, graphics, tables), receive content from server 652, transmit information to server 652, and so on.

In some embodiments, server 652 can include a processor 712, a display 714, one or more inputs 716, one or more communications systems 718, and/or memory 720. In some embodiments, processor 712 can be any suitable hardware processor or combination of processors, such as a CPU, a GPU, and so on. In some embodiments, display 714 can include any suitable display devices, such as a computer monitor, a touchscreen, a television, and so on. In some embodiments, inputs 716 can include any suitable input devices and/or sensors that can be used to receive user input, such as a keyboard, a mouse, a touchscreen, a microphone, and so on.

In some embodiments, communications systems 718 can include any suitable hardware, firmware, and/or software for communicating information over communication network 654 and/or any other suitable communication networks. For example, communications systems 718 can include one or more transceivers, one or more communication chips and/or chip sets, and so on. In a more particular example, communications systems 718 can include hardware, firmware and/or software that can be used to establish a Wi-Fi connection, a Bluetooth connection, a cellular connection, an Ethernet connection, and so on.

In some embodiments, memory 720 can include any suitable storage or devices that can be used to store instructions, values, data, or the like, that can be used, for example, by processor 712 to present content using display 714, to communicate with one or more computing devices 650, and so on. Memory 720 can include any suitable volatile memory, non-volatile memory, storage, or any suitable combination thereof. For example, memory 720 can include RAM, ROM, EEPROM, one or more flash drives, one or more hard disks, one or more solid state drives, one or more optical drives, and so on. In some embodiments, memory 720 can have encoded thereon a server program for controlling operation of server 652. In such embodiments, processor 712 can execute at least a portion of the server program to transmit information and/or content (e.g., data, images, a user interface) to one or more computing devices 650, receive information and/or content from one or more computing devices 650, receive instructions from one or more devices (e.g., a personal computer, a laptop computer, a tablet computer, a smartphone), and so on.

In some embodiments, image source 602 can include a processor 722, one or more image acquisition systems 724, one or more communications systems 726, and/or memory 728. In some embodiments, processor 722 can be any suitable hardware processor or combination of processors, such as a CPU, a GPU, and so on. In some embodiments, the one or more image acquisition systems 724 are generally configured to acquire data, images, or both, and can include an MRI system. Additionally or alternatively, in some embodiments, one or more image acquisition systems 724 can include any suitable hardware, firmware, and/or software for coupling to and/or controlling operations of an MRI system. In some embodiments, one or more portions of the one or more image acquisition systems 724 can be removable and/or replaceable.

Note that, although not shown, image source 602 can include any suitable inputs and/or outputs. For example, image source 602 can include input devices and/or sensors that can be used to receive user input, such as a keyboard, a mouse, a touchscreen, a microphone, a trackpad, a trackball, and so on. As another example, image source 602 can include any suitable display devices, such as a computer monitor, a touchscreen, a television, etc., one or more speakers, and so on.

In some embodiments, communications systems 726 can include any suitable hardware, firmware, and/or software for communicating information to computing device 650 (and, in some embodiments, over communication network 654 and/or any other suitable communication networks). For example, communications systems 726 can include one or more transceivers, one or more communication chips and/or chip sets, and so on. In a more particular example, communications systems 726 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 728 can include any suitable storage device or devices that can be used to store instructions, values, data, or the like, that can be used, for example, by processor 722 to control the one or more image acquisition systems 724, and/or receive data from the one or more image acquisition systems 724; to images from data; present content (e.g., images, a user interface) using a display; communicate with one or more computing devices 650; and so on. Memory 728 can include any suitable volatile memory, non-volatile memory, storage, or any suitable combination thereof. For example, memory 728 can include RAM, ROM, EEPROM, one or more flash drives, one or more hard disks, one or more solid state drives, one or more optical drives, and so on. In some embodiments, memory 728 can have encoded thereon, or otherwise stored therein, a program for controlling operation of image source 602. In such embodiments, processor 722 can execute at least a portion of the program to generate images, transmit information and/or content (e.g., data, images) to one or more computing devices 650, receive information and/or content from one or more computing devices 650, receive instructions from one or more devices (e.g., a personal computer, a laptop computer, a tablet computer, a smartphone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

Figure 8:
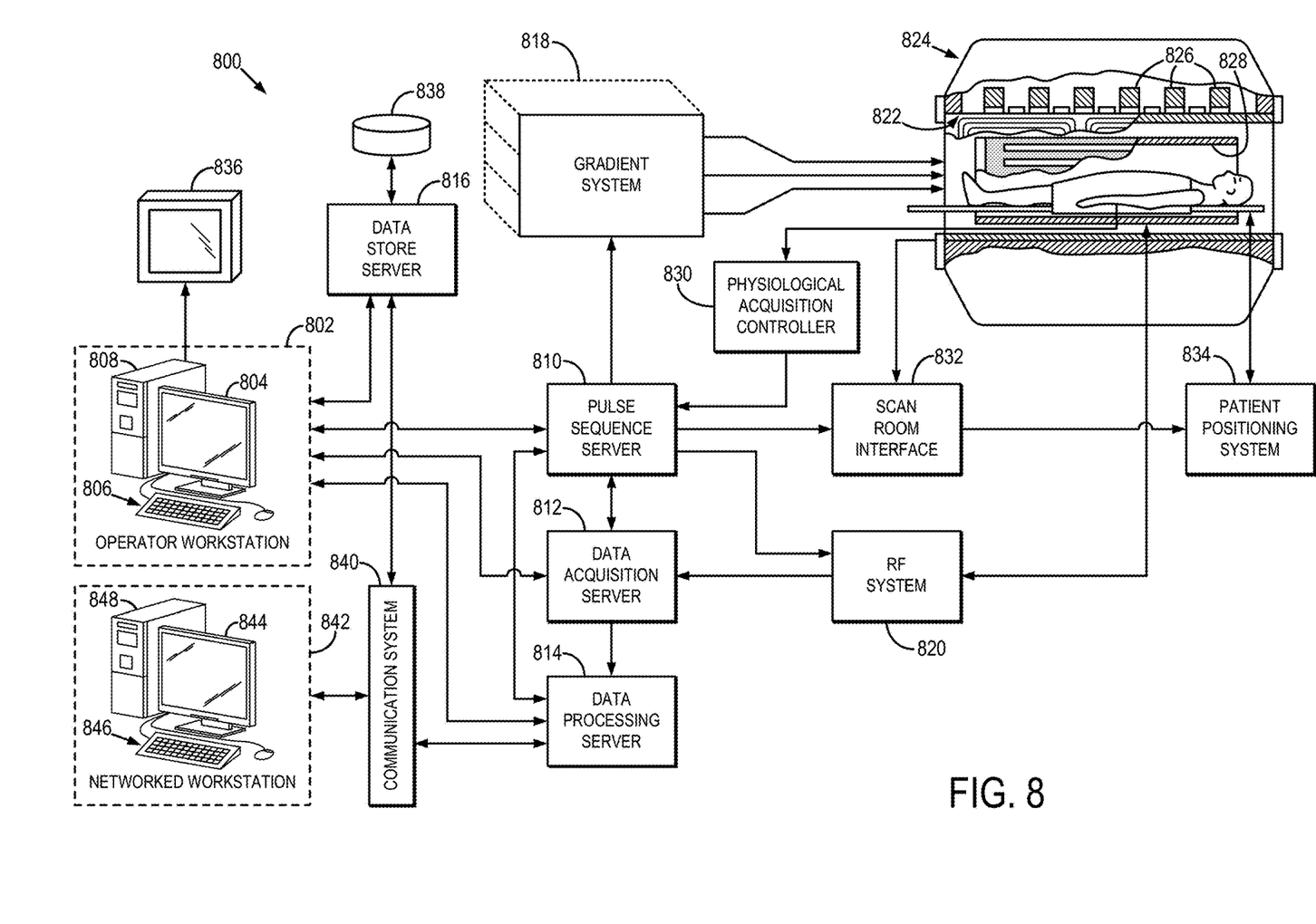
FIG. 8 is a block diagram of an example magnetic resonance imaging system.

Referring particularly now to FIG. 8, an example of an MRI system 800 that can implement the methods described here is illustrated. The MRI system 800 includes an operator workstation 802 that may include a display 804, one or more input devices 806 (e.g., a keyboard, a mouse), and a processor 808. The processor 808 may include a commercially available programmable machine running a commercially available operating system. The operator workstation 802 provides an operator interface that facilitates entering scan parameters into the MRI system 800. The operator workstation 802 may be coupled to different servers, including, for example, a pulse sequence server 810, a data acquisition server 812, a data processing server 814, and a data store server 816. The operator workstation 802 and the servers 810, 812, 814, and 816 may be connected via a communication system 840, which may include wired or wireless network connections.

The pulse sequence server 810 functions in response to instructions provided by the operator workstation 802 to operate a gradient system 818 and a radiofrequency ("RF") system 820. Gradient waveforms for performing a prescribed scan are produced and applied to the gradient system 818, which then excites gradient coils in an assembly 822 to produce the magnetic field gradients $G_x$, $G_y$, and G, that are used for spatially encoding magnetic resonance signals. The gradient coil assembly 822 forms part of a magnet assembly 824 that includes a polarizing magnet 826 and a whole-body RF coil 828.

RF waveforms are applied by the RF system 820 to the RF coil 828, or a separate local coil to perform the prescribed magnetic resonance pulse sequence. Responsive magnetic resonance signals detected by the RF coil 828, or a separate local coil, are received by the RF system 820. The responsive magnetic resonance signals may be amplified, demodulated, filtered, and digitized under direction of commands produced by the pulse sequence server 810. The RF system 820 includes an RF transmitter for producing a wide variety of RF pulses used in MRI pulse sequences. The RF transmitter is responsive to the prescribed scan and direction from the pulse sequence server 810 to produce RF pulses of the desired frequency, phase, and pulse amplitude waveform. The generated RF pulses may be applied to the whole-body RF coil 828 or to one or more local coils or coil arrays.

The RF system 820 also includes one or more RF receiver channels. An RF receiver channel includes an RF preamplifier that amplifies the magnetic resonance signal received by the coil 828 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M = \sqrt{I^2 + Q^2} \tag{1};$$

and the phase of the received magnetic resonance signal may also be determined according to the following relationship:

$$\varphi = \tan^{-1}\left(\frac{Q}{I}\right). \tag{2}$$

The pulse sequence server 810 may receive patient data from a physiological acquisition controller 830. By way of example, the physiological acquisition controller 830 may receive signals from a number of different sensors connected to the patient, including electrocardiograph ("ECG") signals from electrodes, or respiratory signals from a respiratory bellows or other respiratory monitoring devices. These signals may be used by the pulse sequence server 810 to synchronize, or "gate," the performance of the scan with the subject's heart beat or respiration.

The pulse sequence server 810 may also connect to a scan room interface circuit 832 that receives signals from various sensors associated with the condition of the patient and the magnet system. Through the scan room interface circuit 832, a patient positioning system 834 can receive commands to move the patient to desired positions during the scan.

The digitized magnetic resonance signal samples produced by the RF system 820 are received by the data acquisition server 812. The data acquisition server 812 operates in response to instructions downloaded from the operator workstation 802 to receive the real-time magnetic resonance data and provide buffer storage, so that data is not lost by data overrun. In some scans, the data acquisition server 812 passes the acquired magnetic resonance data to the data processor server 814. In scans that require information derived from acquired magnetic resonance data to control the further performance of the scan, the data acquisition server 812 may be programmed to produce such information and convey it to the pulse sequence server 810. For example, during pre-scans, magnetic resonance data may be acquired and used to calibrate the pulse sequence performed by the pulse sequence server 810. As another example, navigator signals may be acquired and used to adjust the operating parameters of the RF system 820 or the gradient system 818, or to control the view order in which k-space is sampled. In still another example, the data acquisition server 812 may also process magnetic resonance signals used to detect the arrival of a contrast agent in a magnetic resonance angiography ("MRA") scan. For example, the data acquisition server 812 may acquire magnetic resonance data and processes it in real-time to produce information that is used to control the scan.

The data processing server 814 receives magnetic resonance data from the data acquisition server 812 and processes the magnetic resonance data in accordance with instructions provided by the operator workstation 802. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 814 are conveyed back to the operator workstation 802 for storage. Real-time images may be stored in a data base memory cache, from which they may be output to operator display 802 or a display 836. Batch mode images or selected real time images may be stored in a host database on disc storage 838. When such images have been reconstructed and transferred to storage, the data processing server 814 may notify the data store server 816 on the operator workstation 802. The operator workstation 802 may be used by an operator to archive the images, produce films, or send the images via a network to other facilities.

The MRI system 800 may also include one or more networked workstations 842. For example, a networked workstation 842 may include a display 844, one or more input devices 846 (e.g., a keyboard, a mouse), and a processor 848. The networked workstation 842 may be located within the same facility as the operator workstation 802, or in a different facility, such as a different healthcare institution or clinic.

The networked workstation 842 may gain remote access to the data processing server 814 or data store server 816 via the communication system 840. Accordingly, multiple networked workstations 842 may have access to the data processing server 814 and the data store server 816. In this manner, magnetic resonance data, reconstructed images, or other data may be exchanged between the data processing server 814 or the data store server 816 and the networked workstations 842, such that the data or images may be remotely processed by a networked workstation 842.

The present disclosure has described one or more preferred embodiments, and it should be appreciated that many equivalents, alternatives, variations, and modifications, aside from those expressly stated, are possible and within the scope of the invention.

The invention claimed is:

1. A method for generating diffusion metric maps from magnetic resonance data, the method comprising:
 (a) accessing with a computer system, magnetic resonance data acquired from a subject, wherein the magnetic resonance data comprise:
  first data that sample k-space with a first k-space sampling and sample q-space with a first q-space sampling;
  second data that sample k-space with a second k-space sampling and sample q-space with a second q-space sampling;
  wherein the first k-space sampling is higher than the second k-space sampling and the first q-space sampling is lower than the second q-space sampling;
 (b) accessing a trained neural network with the computer system, wherein the trained neural network has been trained on training data in order to learn a mapping from magnetic resonance data to diffusion metrics corresponding to at least two different diffusion models; and
 (c) inputting the magnetic resonance data to the trained neural network using the computer system, generating output as a plurality of diffusion metric maps, wherein the plurality of diffusion metric maps depict a spatial distribution in the subject of the diffusion metrics corresponding to the at least two different diffusion models.

2. The method of claim 1, wherein the magnetic resonance data comprise jointly condensed k-q space data in which signal-to-noise tradeoffs are balanced by increasing k-space sampling for lower diffusion weighting b-values and increasing q-space sampling for lower spatial resolution acquisitions.

3. The method of claim 1, wherein accessing the magnetic resonance data comprises acquiring the magnetic resonance data with a magnetic resonance imaging (MM) system and communicating the magnetic resonance data to the computer system.

4. The method of claim 1, wherein the trained neural network comprises a convolutional neural network (CNN).

5. The method of claim 4, wherein the CNN is a three-dimensional deep CNN.

6. The method of claim 5, wherein the three-dimensional deep CNN is a three-dimensional deep residual network (ResNet) CNN.

7. The method of claim 1, wherein the magnetic resonance data comprise diffusion-weighted magnetic resonance images reconstructed from the first data and the second data.

8. The method of claim 7, wherein the diffusion-weighted magnetic resonance images are reconstructed from a combined dataset generated by combining the first data and the second data.

9. The method of claim 8, wherein the combined dataset is generated by combining the first data and the second data using a spatially variant weighting of the first data and the second data.

10. The method of claim 1, wherein the at least two different diffusion models are selected from the group consisting essentially of a diffusion tensor imaging model, a neurite orientation dispersion and density imaging model, a spherical mean technique micro-diffusion tensor model, and a spherical mean technique multi-compartment microstructural imaging model.

11. The method of claim 1, wherein one of the at least two different diffusion models is a diffusion tensor imaging model and the diffusion metrics comprise at least one of fractional anisotropy, mean diffusivity, axial diffusivity, or radial diffusivity.

12. The method of claim 1, wherein one of the at least two different diffusion models is a neurite orientation dispersion and density imaging model and the diffusion metrics comprise at least one of fraction of water in a restricted compartment, fraction of water in an isotropic compartment, orientation dispersion index, or hindered volume fraction.

13. The method of claim 1, wherein one of the at least two different diffusion models is a spherical mean technique micro-diffusion tensor model and the diffusion metrics comprise at least one of fractional anisotropy, mean diffusivity, or radial diffusivity.

14. The method of claim 1, wherein one of the at least two different diffusion models is a spherical mean technique multi-compartment microstructural imaging model and the diffusion metrics comprise at least one of intra-axonal water fraction, extra-neurite microscopic mean diffusivity, extra-neurite transverse microscopic diffusivity.

15. A method for generating diffusion metric maps from magnetic resonance data acquired with a magnetic resonance imaging (MM) system, the method comprising:

(a) acquiring diffusion-weighted magnetic resonance data from a subject with the MRI system, wherein the diffusion-weighted magnetic resonance data jointly sample k-q space such that k-space sampling is increased at lower diffusion weighting b-values and q-space sampling is increased at lower spatial resolutions;

(b) reconstructing diffusion-weighted images from the diffusion-weighted magnetic resonance data using a computer system;

(c) accessing a trained neural network with the computer system, wherein the trained neural network has been trained on training data in order to learn a mapping from diffusion-weighted images to diffusion metrics corresponding to at least two different diffusion models; and (d) inputting the diffusion-weighted images to the trained neural network using the computer system, generating output as a plurality of diffusion metric maps, wherein the plurality of diffusion metric maps depict a spatial distribution in the subject of the diffusion metrics corresponding to the at least two different diffusion models.

16. The method of claim 15, wherein the diffusion-weighted images consist of a non-diffusion weighted image acquired with a zero diffusion weighting b-value and nine diffusion-weighted images acquired with a non-zero diffusion weighting b-value.

17. The method of claim 16, wherein the nine diffusion-weighted images include three images acquired at each of three different non-zero diffusion weighting b-values.

18. The method of claim 15, wherein the diffusion-weighted magnetic resonance data are acquired over a range of diffusion weighting b-values spanning 0 mm/s$^2$ to 8,000 mm/s$^2$.

19. The method of claim 15, wherein the at least two different diffusion models are selected from the group consisting essentially of a diffusion tensor imaging model, a neurite orientation dispersion and density imaging model, a spherical mean technique micro-diffusion tensor model, and a spherical mean technique multi-compartment microstructural imaging model.

* * * * *

UNITED STATES PATENT AND TRADEMARK OFFICE
CERTIFICATE OF CORRECTION

| | |
|---|---|
| PATENT NO. | : 12,044,762 B2 |
| APPLICATION NO. | : 17/166734 |
| DATED | : July 23, 2024 |
| INVENTOR(S) | : Qiuyun Fan et al. |

Page 1 of 1

It is certified that error appears in the above-identified patent and that said Letters Patent is hereby corrected as shown below:

In the Claims

Claim 3, Line 61, Column 14, "data with a magnetic resonance imaging (MM) system and" should be --data with a magnetic resonance imaging (MRI) system and--

Claim 15, Line 46, Column 15, "nance imaging (MM) system, the method comprising:" should be --nance imaging (MRI) system, the method comprising:--

Signed and Sealed this
Twenty-second Day of April, 2025

Coke Morgan Stewart
*Acting Director of the United States Patent and Trademark Office*